United States Patent [19]

McDonald

[11] 4,046,508
[45] Sept. 6, 1977

[54] SANITARY HANDLE

[76] Inventor: William M. McDonald, 7116 Woodmore Oaks, Citrus Heights, Calif. 95610

[21] Appl. No.: 696,553

[22] Filed: June 16, 1976

[51] Int. Cl.² .............................................. A61L 3/00
[52] U.S. Cl. .................................... 21/77; 4/222
[58] Field of Search ............ 21/77, 2, 103, 58; 292/347, 1; 4/222

[56] References Cited

U.S. PATENT DOCUMENTS

| 694,119 | 2/1902 | Von Stryk | 4/222 |
| 2,044,904 | 6/1936 | Heisig | 4/222 X |
| 2,561,861 | 7/1951 | Held | 21/77 |
| 3,042,981 | 7/1962 | Dilione | 21/77 |
| 3,192,008 | 6/1965 | Dwyer | 4/222 X |
| 3,344,959 | 10/1967 | Fasp | 21/77 UX |

Primary Examiner—Morris O. Wolk
Assistant Examiner—Arnold Turk
Attorney, Agent, or Firm—Blair & Brown

[57] ABSTRACT

A sanitary door handle for the inside of a public toilet door which includes a generally circular handle element having means for rotating the handle to a new position with the handle being moved through a sterilizing bath as it rotates. Means are provided for effecting rotation of the handle on each opening of the door.

4 Claims, 6 Drawing Figures

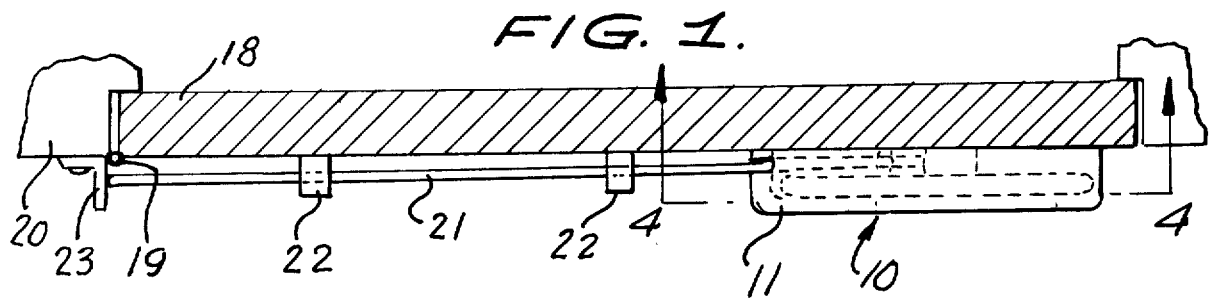
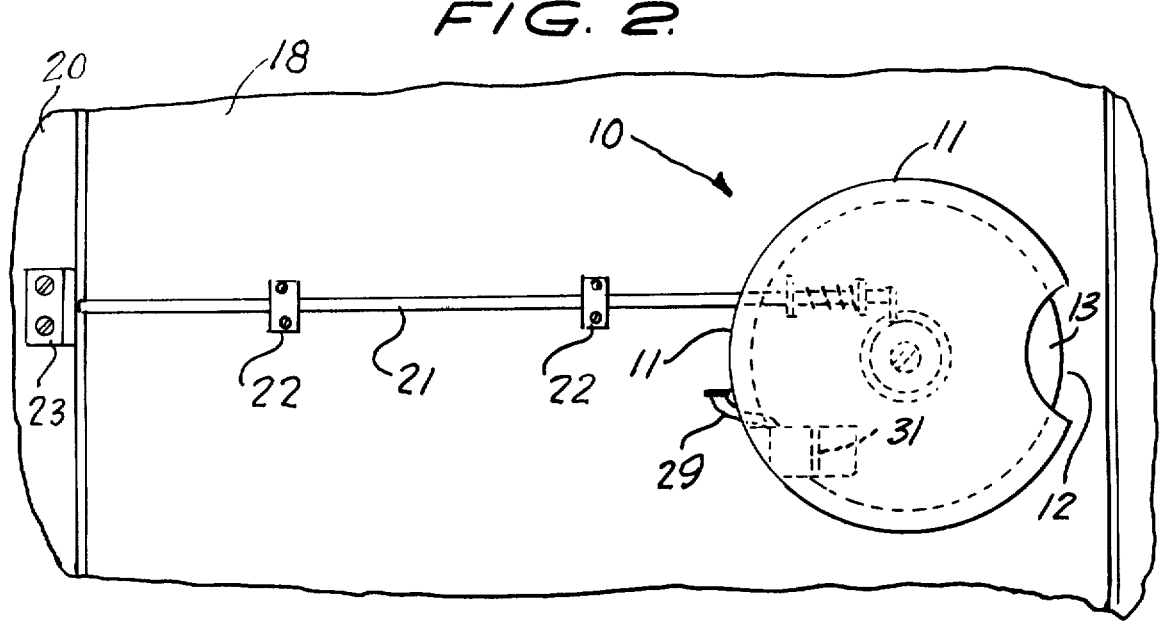
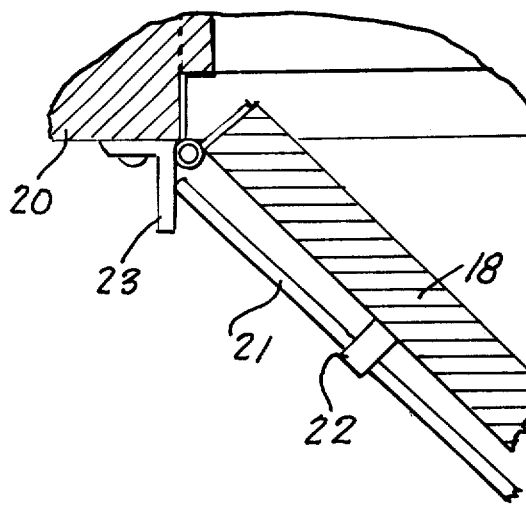

SANITARY HANDLE

BACKGROUND OF THE INVENTION

Field of the Invention

The present invention relates to a door handle which is sanitized after each use.

In public rest rooms it often appears that persons with unclean habits use the facilities without washing their hands. It is necessary of course to have the doors to the toilets and wash rooms be hand operated. The present invention has for its principle object to provide a sanitary means to open a door to such facilities.

Other objects and advantages will appear in the following specification when taken in light of the attached drawings.

BRIEF DESCRIPTION OF THE DRAWINGS

FIG. 1 is a plan view of the invention mounted on a door with the door being shown in section;

FIG. 2 is an elevation of the device mounted on a door;

FIG. 3 is a fragmentary plan view similar to FIG. 1 of the ratchet operating device with the door in partly open position;

DESCRIPTION OF THE PREFERRED EMBODIMENT

Figure 4:
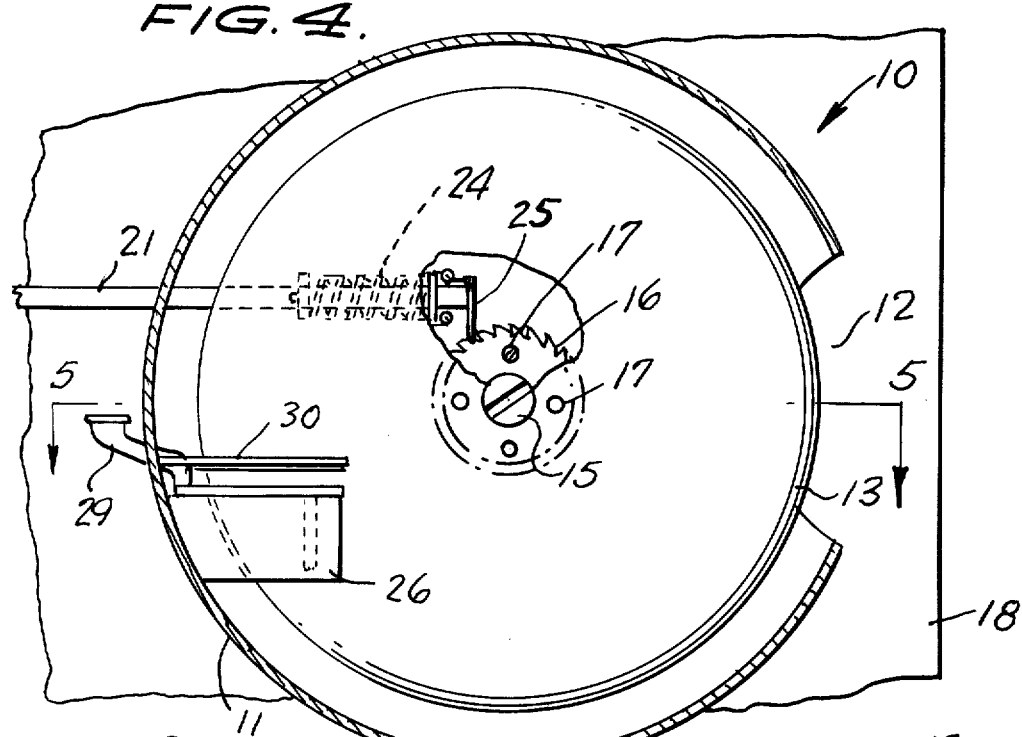
FIG. 4 is a horizontal sectional view taken along the line 4—4 of FIG. 1 looking in the direction of the arrows.

Referring now to the drawings in detail wherein like reference characters indicate like parts throughout the several figures, the reference numeral 10 indicates generally a sanitary door operator constructed in accordance with the invention.

Figure 5:
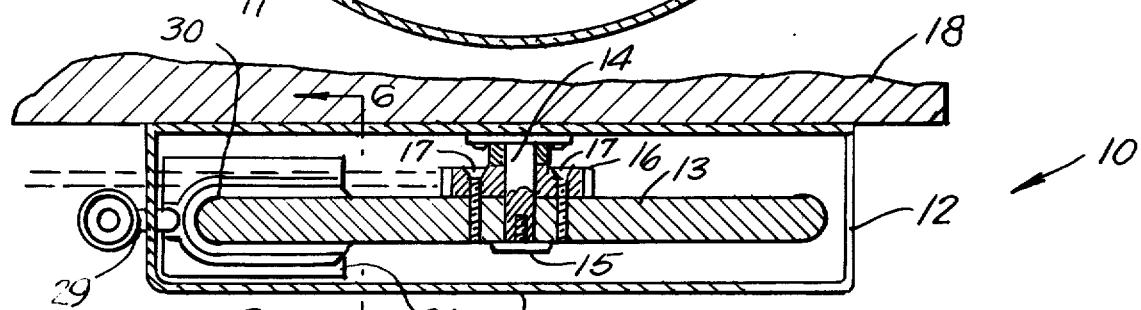
FIG. 5 is a horizontal sectional view taken along the line 5—5 of FIG. 4 looking in the direction of the arrows.
Figure 6:
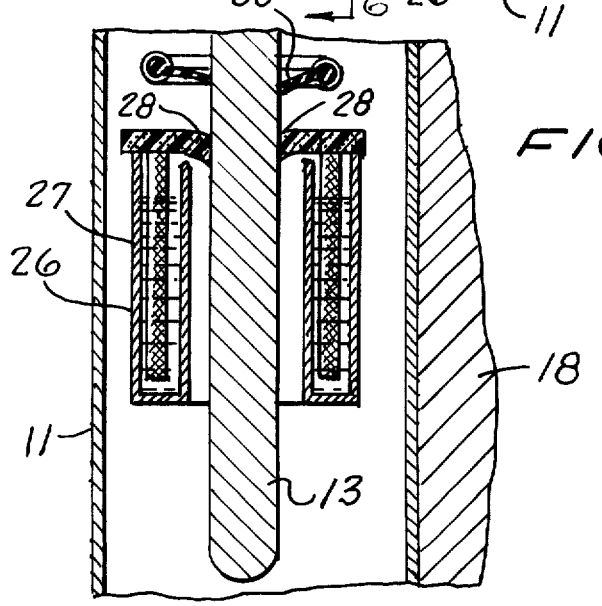
FIG. 6 is a fragmentary enlarged sectional view taken along the line 6—6 of FIG. 5 looking in the direction of the arrows.

The operator 10 includes a housing 11 of generally circular form having an aperture 12 in one side thereof. A wheel 13 is positioned within the housing on a shaft 14 secured thereto by a screw 15. A circular rack 16 is secured to the wheel 13 by a plurality of screws 17 as can be best seen in FIGS. 4 and 5.

The housing 11 is secured to a door 18 hinged at 19 to a frame 20 positioned to give access to a restroom. The door 18 is secured in closed position by any suitable latch (not shown).

An actuator rod 21 is secured in guides 22 on the door 18 and engages against the bracket 23 secured to the frame 20. The actuator rod 21 extends into the housing 11 and a coil spring 24 normally urges the rod 21 in a direction toward the bracket 23. A hinged pawl 25 on the end of the rod 21 engages with the rack 16 to rotate the shaft 14 each time the door 18 is opened. Opening of the door 18 causes the actuator rod 21 to be moved to the right against the tension of the spring 24 to rotate the shaft 14 a desired distance.

A generally U-shaped tank 26 is mounted in the housing 11 and extends onto opposite sides of the wheel 13. The U-shaped tank 26 has a U-shaped wick 27 immersed therein and extending to a horizontal portion 28 of the wick which engages opposite sides of the wheel 13. A filler pipe 29 is connected to the tank 26 to permit the sanitizing chemicals therein to be replenished. A rubber squeegee scraper 30 engages opposite sides of the wheel 13 above the tank 26 so as to remove excess sanitizing fluid from the wheel 13 as the wheel 13 is rotated in a clockwise direction thereby.

The tank 26 is formed of transparent plastic material and a slot 31 in the housing 11 permits the contents of the tank 26 to be viewed so as to determine if refilling is required.

In the use and operation of the invention the user of the invention grasps the wheel 13 to open the door 18 and then as the door 18 swings inwardly the actuator rod 21 is moved to the right by the bracket 23 thus rotating the shaft 14 in a clockwise direction so that wheel 13 will pass through the sanitizing wicks 28 and the squeegee scraper 30. It can be thus seen that the wheel 13 is continuously treated to sterilize any bacteria that would otherwise be found thereon.

Having thus described the preferred embodiment of the invention is should be understood that numerous structural modifications and adaptations may be resorted to without departing from the spirit of the invention.

What is claimed is:

1. A sterilized door handle apparatus comprising a housing secured to a door and having an aperture in one side thereof, a wheel rotatably mounted in said housing and having a portion thereof graspable through said aperture for opening the door, means in said housing engaging said wheel for coating said wheel with sterilizing liquids, means in said housing adjacent said last named means for removing excess liquid from said wheel, and means on said door engaging means on its door frame for rotationally advancing said wheel each time the door is opened.

2. A device as claimed in claim 1 wherein the means for coating said wheel with a sterilizing liquid comprises a generally U-shaped tank, a wick in said tank and engaging opposite sides of said wheel, and means extending from said tank out of said housing for filling said tank with sterilizing fluids.

3. A device as claimed in claim 2 wherein said tank is of transparent plastic and said housing is provided with a slot through which the contents of said tank might be viewed.

4. A device as claimed in claim 1 wherein the means for advancing said wheel includes a circular ratchet on said wheel and a hinged pawl engaging said ratchet and actuated by opening of said door.

* * * * *